United States Patent [19]
Dombay et al.

[11] Patent Number: 4,670,429
[45] Date of Patent: Jun. 2, 1987

[54] SYNERGISTIC FUNGICIDAL COMPOSITIONS

[75] Inventors: Zsolt Dombay; Erzsébet Grega née Tóth; József Nagy, all of Miskolc; Csaba Pavliscsák, Sajóbábony; Lászlo Tasi; András Tóth, both of Miskolc; Oszkár Tóth, Debrecen; Judit Vitányi, Miskolc; Ferenc Bihari, Budapest; Péter Bohus, Budapest; Péter Inczédy, Budapest; István Magyari, Gödöllo; Marianna Kertész née Szabó, Budapest; László Wohl, Budapest; Attila Ferenczi, Budapest, all of Hungary

[73] Assignees: Eszakmagyarorszagi Vegyimuvek; Budapesti Vegyimuvek, both of Budapest, Hungary

[21] Appl. No.: 633,380

[22] Filed: Jul. 23, 1984

[30] Foreign Application Priority Data

Jul. 21, 1983 [HU] Hungary .............................. 2566/83

[51] Int. Cl.⁴ ...................... A01N 55/02; A01N 43/32
[52] U.S. Cl. ..................................... 514/187; 514/433
[58] Field of Search ................................ 514/433, 187

[56] References Cited

U.S. PATENT DOCUMENTS 3,249,499  5/1966  Von Schmeling et al. ......... 514/433
3,402,241  9/1968  Von Schmeling et al. ......... 514/433
4,086,339  4/1978  Matolcsy et al. ................... 514/187

OTHER PUBLICATIONS

Chemical Abstracts, vol. 86 (1977) #29607q; Matolesy et al.

Primary Examiner—Leonard Schenkman
Assistant Examiner—Joseph A. Lipovsky
Attorney, Agent, or Firm—Karl F. Ross; Herbert Dubno

[57] ABSTRACT

The invention relates to a synergistic fungicidal composition containing more active ingredients comprising 2,3-dihydroxy-6-methyl-5-phenylcarbamoyl-1,4-oxathiine or 2.3-dihydro-6-methyl-5-phenylcarbamoyl-1,4-oxathiine-4,4-dioxide and the zinc and manganese complexes of (8-oxyquinolinate)-(dimethyl dithiocarbamate) as active ingredients, optionally solid and/or liquid carriers and other excipients. The compositions is of value especially in the treatment of infections caused by ustilaginales and yellow rust on cereals.

8 Claims, No Drawings

SYNERGISTIC FUNGICIDAL COMPOSITIONS

FIELD OF THE INVENTION

The invention relates to synergistic fungicidal compositions comprising several active ingredients used in the treatment of fungal diseases of cereals, especially infections caused by smuts (ustilaginales), yellow rust of cereals. The invention also discloses a method for combatting or preventing fungal infections by applying the said composition to the locus of the infection.

BACKGROUND OF THE INVENTION

It is well known from the art, that the most important pathogenic fungi of cereals (e.g. wheat, barley) are as follows:

smut diseases, such as bunt smut of wheat (*Tilletia foetida*), loose smut of barley (*Ustilago nuda*) and the fusarium species (Fusarium spp.) which infect the plant at the embryo stage partly in the soil, partly internally in the seed;

powdery mildew species (e.g. *Erypsiphe graminis*) which attack the plant at various stages during its life;

cereal fusarium fungi (*Fusarium graminearum*) and rusts (e.g. *Puccinia glumarum*) which attack the corn after earing.

The infections of the plant germs are treated by seed-dressing, while the later fungal attacks are treated with foliar spray application of different kinds of fungicides.

So far mercury containing compounds have been used for seed-dressing of corn. However, these compounds have several disadvantages. The health-detrimental and accumulating effect of mercury containing compounds is well known and the compounds do not protect the seeds from internal infections either.

Thus new fungicidal agents have become necessary, which are at least so effective as the mercury containing substances but are not that toxic.

U.S. Pat. Nos. 3,249,499, 3,393,202 and 3,454,391 and FR Pat. Nos. 1 477 059 and 1 477 060 disclose 2,3-dihydro-5-carboxamido-6-methyl-1,4-oxathiines as fungicidal agents.

In FR Pat. Nos. 1 477 061 and 1 477 062 and U.S. Pat. Nos. 3,402,241 and 3,454,391 derivatives are described in which in the ring one or two oxygens are attached to the sulphur atom, i.e. sulfoxides and sulfones. The utility of oxathiines for protection of plants and seeds against plant pathogenic fungi is mentioned. A disadvantage, however is their inefficiency against several species, such as Penicillium sp., *Septaria nodorum* etc.

In Hungarian patent specification No. 171,736 the very favorable fungicidal effect of the mixed liganded (8-oxyquinolate)-(dimethyl dithiocarbamate) metal complexes are described. Said metal complexes are always more effective—especially if the central atom is zinc, manganese, copper, magnesium, iron, cadmium etc.—than the metal complexes of either 8-oxyquinolate or dimethyl dithiocarbamate comprising the same ligand. It is further reported, that a mixture containing 1 part by weight of zinc complex and 1 part by weight of manganese complex is preferred.

According to HU-PS 158 608 the fungicidal spectrum off 2,3-dihydro-5-carboxanilid-6-methyl-1,4-oxathiines can be considerably broadened and in many cases an unexpected synergistic activity can be achieved by combining a salt or ester of 8-hydroxyquinoline, such as copper salt thereof, e.g. copper-8-quinolinolate, or its sulphate or benzoate and said oxathiines. Particularly good result was achieved by combining copper-8-quinolinate and carboxanilide-oxathiine at a ratio of 1:15–3:5 against fungi belonging to Basidiomycetes, such as Rhizoctonia Kuhl and *Uromyces phasecoli typica* Arth (plant pathogen, fungi in soil). These fungicidal agents were especially effective against inner fungi in the seeds of cereals, transferred by seeds, such as *Ustilago nuda*, against which only hot-water treatment proved to be efficient earlier. No biological activity test result was included in the specification and activity of this composition was confirmed only against *Septoria nodorum*, *Fusarium nivale* and Penicillium sp.

SUMMARY OF THE INVENTION

The composition according to the invention contains 2,3-dihydroxy-6-methyl-5-phenylcarbamoyl-1,4-oxathiine (Carboxin) or 2,3-dihydro-6-methyl-5-phenylcarbamoyl-1,4-oxathiine-4,4-dioxide (Oxicarboxin) and zinc and manganese complexes of (8-oxyquinolate)-(dimethyl dithiobarbamate) as active ingredients in a weight ratio of 1:3 to 3:1 and the weight ratio of the two different metal complexes of (8-oxyquinolinate)-(dimethyl dithiocarbamate) is 1:1.

The composition preferably contains 5% to 90% by weight of active ingredients, as well as solid or liquid carriers and other excipients.

According to a second aspect of the invention, there is provided a method of treating fungal infections of plants which comprises applying to said plants a fungicidally effective amount of a fungicidal formulation as defined above.

DETAILED DESCRIPTION OF THE INVENTION

The combinations of active ingredients defined in the above formulation are novel and have been found to be surprisingly effective in controlling or combatting fungal infections of cereals.

The composition exhibits synergistic effect in the range of a weight ratio of and the metal complexes being 1:3 to 3:1. The preferred weight ratio of the two metal complexes is 1:1.

In the method of treating fungal infections the formulation can be applied by foliar application or it can be used as seed-dresser depending on the fungal attack to be treated. The amount and frequency of application is determined by the severity or expected severity of the fungal disease and, as is well known to those skilled in the art, by the age and condition of the crop.

In order to simplify manufacture, storage and transport, the combinations of the active ingredients are normally produced in a concentrate or powder from intended for dilution in a solvent to the degree necessary to enable the above mentioned application rates to be easily achieved. Such formulations are usually in the form of a wettable powder or dust, aqueous or oily suspension, emulsifiable concentrate and granules. The concentrate formulations are intended for appropriate dilution prior to use. This formation of a dispersion can be carried out in conventional spray tanks suitable for the purpose.

Wettable powders or dusts comprise an intimate mixture of the active ingredients, one or more inert carriers and appropriate excipients. The inert carrier may be selected from the attapulgite clays, the montmorillonite clays, the diatomaceous earths, kaolins, micas, talcs and purified silicates.

Sufficient excipients may be found among the non-ionic and ionic surfactants. E.g. sodium or calcium salts of polyacrylic acids and lignin sulphonic acid; the condensation of fatty acids or aliphatic amines or amides with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols with ethylene oxide and/or propylene oxide; sulphates or sulphonates of these condensation products; alkali or alkaline earth metals of sulphuric or sulphonic acid esters; sodium alkylaryl sulphonates; polymers of ethylene oxide and copolymers of ethylene oxide and propylene oxide.

The composition according to the invention can be used most preferably in the form of an aqueous dispersion which active ingredient concentration depends on the manner of application, i.e. foliar application or seed-dressing.

The invention is illustrated by the following, non-limiting examples.

EXAMPLE 1

A seed-dressing suspension concentrate containing a film forming polymer is prepared with a total active ingredient concentration of 300 g/1000 ml by admixing the components given in Table 1. The solution containing solid particles is wet-milled until the diameter of the solid particles is less than 4 micron.

The combination can preferably be used for wet seed-dressing.

TABLE 1

| Compound | Amount of the compound added to the composition (g). | | | | | | | | | | |
|---|---|---|---|---|---|---|---|---|---|---|---|
| Carboxin | 300 | — | — | — | — | 75 | 100 | 150 | 200 | 225 | |
| (8-oxyquinolate)-(dimethyl dithio-carbamate) Zn complex | — | 300 | — | 75 | 150 | 225 | 112.5 | 100 | 75 | 50 | 37.5 |
| (8-oxyquinolate)-(dimethyl dithio-carbamate) Mn complex | — | — | 300 | 225 | 150 | 75 | 112.5 | 100 | 75 | 50 | 37.5 |
| ethyleneglycol | 90 | 90 | 90 | 90 | 90 | 90 | 90 | 90 | 90 | 90 | 90 |
| Tamol MD | 40 | 40 | 40 | 40 | 40 | 40 | 40 | 40 | 40 | 40 | 40 |
| Pluriol PE 10500 | 20 | 20 | 20 | 25 | 25 | 25 | 30 | 30 | 30 | 30 | 30 |
| Poligen ASN | 150 | 150 | 150 | 150 | 150 | 150 | 150 | 150 | 150 | 150 | 150 |
| Rhodamin 2BU Plu | 5 | 5 | 5 | 5 | 5 | 5 | 5 | 5 | 5 | 5 | 5 | ion exchanged water filled to 1000 ml.

EXAMPLE 2

A formulation containing a total 400 g/1000 ml of active ingredients is prepared. The combination of the composition is shown by Table 2. After the compounds are charged, the composition is filled with ion exchanged water to 1000 ml. and wet-milled until the particle size in the suspension achieves the size not higher than 5 micron.

The formulation is applied by foliar spray application after earing of corn.

Similarly were prepared the suspensions containing active ingredients separately for comparative tests.

TABLE 2

| Compounds | Charged amounts of the compounds (g) | | | | | | | | | | |
|---|---|---|---|---|---|---|---|---|---|---|---|
| Oxicarboxin | 400 | — | — | — | — | — | 100 | 133.4 | 200 | 266.7 | 300 |
| (8-oxyquinolate)-(dimethyl di-thiocarbamate) Zn complex | — | 400 | — | 100 | 200 | 300 | 150 | 133.3 | 100 | 66.65 | 50 |
| (8-oxyquinolate)-(dimethyl dithio-carbamate) Mn complex | — | — | 400 | 300 | 200 | 100 | 150 | 133.3 | 100 | 66.65 | 50 |
| ethyleneglycol | 80 | 80 | 80 | 80 | 80 | 80 | 80 | 80 | 80 | 80 | 80 |
| Borresperse 3A | 40 | 40 | 40 | 40 | 40 | 40 | 45 | 45 | 45 | 45 | 45 |
| Tensiofix CD 5 | 15 | 15 | 15 | 15 | 15 | 15 | 10 | 10 | 10 | 10 | 10 |
| Rhodopol 23 | 0.1 | 0.1 | 0.1 | 0.1 | 0.1 | 0.1 | 0.1 | 0.1 | 0.1 | 0.1 | 0.1 |
| Bentonit | 0.15 | 0.15 | 0.15 | 0.15 | 0.15 | 0.15 | 0.1 | 0.1 | 0.1 | 0.1 | 0.1 |

EXAMPLE 3

Wettable powder of 80–90% by weight of total active ingredients is prepared for dressing of seeds of cereals pea and potato. The compounds are charged in an amount shown by Table 3, the composition is mixed, homogenized and milled until the size of the particles is 4 micron.

TABLE 3

| Compounds | Charged amounts of the compounds (g) | | | |
|---|---|---|---|---|
| Carboxin | 22.5 | 40 | 30 | 60 |
| (8-oxyquinolate)-(dimethyl di-thiocarbamate) Zn complex | 33.75 | 20 | 30 | 15 |
| (8-oxyquinolate)-(dimethyl dithio-carbamate) Mn complex | 33.75 | 20 | 30 | 15 |
| Zeolex 444 | 6 | 16 | 6 | 6 |
| Netzer IS | 1.5 | 1.5 | 1.5 | 1.5 |
| Dispersing agent 1494 | 2.5 | 2.5 | 2.5 | 2.5 |

EXAMPLE 4

Wettable powder suitable for use in foliar application of field crops, mainly cereals were prepared. The amounts of the compounds charged are listed in Table 4.

The concentration of the active ingredients in the compositions were 5, 15 20 and 50% by weight. The substances were homogenized and milled as described in Example 3, until a particle size of 4 micron.

TABLE 4

| Compounds | Amounts of the compounds charged (g) | | | |
|---|---|---|---|---|
| Carboxin | 1.5 | 10 | 15 | 25 |
| a 1:1 mixture of Zn and Mn complexes of (8-oxyquinolate)-(dimethyl dithiocarbamate) | 3.5 | 5 | 5 | 25 |
| Zeolex 444 | 10 | 10 | 10 | 10 |
| silica earth | 78 | 68 | 60 | 33 |
| Netzer IS | 2 | 2 | 3 | 2 |
| sulfit lye powder | 5 | 5 | 7 | 5 |

EXAMPLE 5

Against pathogenic fungi damaging the crop plants after earing compositions for use in foliar application are prepared with a total active ingredient content of 5, 10, 15 and 20% by weight by admixing substances shown in Table 5 and stirring until all the solid material is dissolved.

TABLE 5

| Compound | Amounts of the charged compounds (g) | | | |
|---|---|---|---|---|
| Carboxin | 3 | 5 | 5 | 10 |
| an 1:1 mixture of Zn and Mn complexes of (8-oxyquinolate)-(dimethyl dithiocarbamate) | 2 | 5 | 15 | 5 |
| xylene | 67 | 62 | 50 | 55 |
| dimethyl sulfoxide | 20 | 20 | 20 | 20 |
| Tensiofix AS | 5 | 5 | 5 | 5 |
| Tensiofix IS | 3 | 3 | 5 | 5 |

EXAMPLE 6

Seed dressing of spring barley against *Ustilago nuda* (loose smut of barley).

The test was performed on 100 m² plots in three replicates by using Fertodi 053 type seeds subjected to wet-dressing, using compositions disclosed in Example 1, and seeding was performed on March 17. The dressing agents contained 300 g/l active ingredient (total), and the used amount was 5 l/t seed.

Part of the seeds was not treated, as these served as control. The efficiency of the dressing agents was determined between June 5 to 10 by counting the ears infected by loose smut. The results are shown in Table 6.

TABLE 6

| Treatment | Dose g/t | | | Active ingredient ratio | Ears infected by loose smut per plot (average pieces) |
|---|---|---|---|---|---|
| | Carboxin | Zn | Mn | | |
| Carboxin | 1500 | — | — | — | 165 |
| zinc complex | — | 1500 | — | — | 376 |
| manganese complex | — | — | 1500 | — | 398 |
| mixture of zinc and manganese complex | — | 375 | 1125 | 1:3 | 274 |
| | — | 750 | 750 | 1:1 | 235 |
| | — | 1125 | 375 | 3:1 | 282 |
| composition according to the invention | 375 | 562.5 | 562.5 | 1:3 | 147 |
| | 500 | 500 | 500 | 1:2 | 98 |
| | 750 | 375 | 375 | 1:1 | 51 |
| | 1000 | 250 | 250 | 2:1 | 33 |
| | 1125 | 187.5 | 187.5 | 3:1 | 60 |
| untreated control | — | — | — | — | 3114 |

The table shows that the 1:3–3:1 mixture of carboxin and (8-oxyquinolinate)-dimethyl-dithiocarbamate Zn and Mn complexes exhibit synergistic activity and a protective activity when using 1500 g/t against infection by loose smut of spring barley.

EXAMPLE 7

The test shows the protective activity of the combinations on winter wheat against yellow rust (*Puccinia glumarum*). The tested combinations were applied as foliar sprays in field tests.

NS-Róna 2 type wheat seeds were seeded on plots of 5 ha. on October 25th into the soil adequately prepared.

The well emerged plants saved from winterkill were weed controlled by a herbicide containing MCPA as active ingredient, generally used in cultivation of cereals by spraying by airoplane, thereafter a sulphur comprising formulation (Sulphur 900 FW) was applied as a foliar spray at the end of tillage (on 5th May) in order to supress the incipient (powdery mildew) infection.

Later the selected plots were treated the first time at the end of earing (on 30th May), when the first signs of yellow rust were already observed. In the treatment Oxicarboxin, zinc and manganese complexes of (8-oxyquinolate)-(dimethyl dithiocarbamate) and the combination according to the invention were used in 400 FW formulation, described in Example 2. 50 l/ha. of water were used for spraying, the amount of the active ingredients applied was 0.75 to 1.5 kg/ha.

The efficiency of the combinations against yellow rust was evaluated on 12th June. 100 productive plants selected by randomised method from each plots were examined, and the infection index was determined according to the following scale:

0 = symptom-free
1 = the infection is 5% or less
2 = the infection is within the range of from 6% to 10%
3 = the infection is within the range of from 11% to 25%
4 = the infection is within the range of from 26% to 50%
5 = the infection is within the range of from 51% to 75%
6 = the infection is within the range of from 76% to 100%

The percent of the infection expresses the rate of the healthy and infected leaf surfaces or the average coverage of the leaf surface of the four leaf nodes by mycelium.

The infection index was calculated from the data obtained according to the following formula:

$$F_i = (a_i \cdot f_i)/n$$

wherein $a_i$ stands for the infection values according to the above scale, $f_i$ represents the frequency of a certain scale value, while n stands for the number of the plants examined.

The experimental results are listed in Table 7.

The thus prepared seeds were seed-dressed with a combination according to Example 3 at a dosage of 900 g/t.

Further seed-dressing liquids were prepared containing only carboxin or only zinc or manganese complexes of (8-oxyquinolate)-(dimethyl-dithiocarbamate). The compositions were similarly prepared as in Example 3. As comparative formulation Quinolate V-4X was used in an amount of 900 g/t. This formulation contained 50% Carboxin and 15% copper oxyquinolate as active ingredient.

A part of the infected seeds was not seed-dressed and served as control in the experiments.

2×100 pieces of the treated and untreated seeds were

TABLE 7

| Treatment | Dosage kg/ha. | | | Rate of the active ingredients | Number of the infected plants belonging to each scale values | | | | | | | $F_1$ |
|---|---|---|---|---|---|---|---|---|---|---|---|---|
| | Oxicarboxin | Zn | Mn | | 0 | 1 | 2 | 3 | 4 | 5 | 6 | |
| Oxicarboxin | 0.75 | — | — | — | 18 | 29 | 34 | 19 | — | | | 1.54 |
| | 1.50 | — | — | — | 36 | 28 | 23 | 13 | — | | | 1.13 |
| zinc complex | — | 0.75 | — | — | — | 12 | 58 | 18 | 12 | | | 2.30 |
| | — | 1.50 | — | — | — | 36 | 35 | 22 | 7 | | | 2.00 |
| manganese | — | — | 0.75 | — | — | 10 | 57 | 19 | 14 | | | 2.37 |
| complex | — | — | 1.50 | — | — | 36 | 33 | 23 | 8 | | | 2.03 |
| the mixture of | — | 0.375 | 1.125 | 1:3 | 5 | 36 | 33 | 20 | 6 | | | 1.86 |
| the zinc and | — | 0.75 | 0.75 | 1:1 | 10 | 32 | 32 | 21 | 5 | | | 1.79 |
| manganese complexes | — | 1.125 | 0.375 | 3:1 | — | 37 | 34 | 24 | 5 | | | 1.97 |
| the composition | 0.375 | 0.562 | 0.563 | 1:3 | 43 | 25 | 21 | 8 | 3 | | | 1.03 |
| according to | 0.5 | 0.5 | 0.5 | 1:2 | 53 | 32 | 14 | 1 | — | | | 0.63 |
| the invention | 0.75 | 0.375 | 0.375 | 1:1 | 54 | 31 | 15 | — | — | | | 0.61 |
| | 1.0 | 0.25 | 0.25 | 2:1 | 52 | 23 | 17 | 8 | — | | | 0.81 |
| | 1.125 | 0.187 | 0.188 | 3:1 | 48 | 25 | 18 | 9 | — | | | 0.88 |
| untreated control | — | — | — | — | — | 15 | 15 | 22 | 20 | 10 | 18 | 3.49 |

The test results very expressively show that hte combinations containing oxicarboxin, zinc and manganese complexes of (8-oxyquinolinate)-(dimethyl-dithiocarbamate) at the weight ratio of 1:3 to 3:1 can adequately prevent the yellow rust infection of winter wheat and exhibit a synergistic effect in these ratios of the active ingredients.

EXAMPLE 8

This Example illustrates the typical synergistic activity observed when combinations of the invention are employed for control of fungal organisms, such as Fusarium spp. and Tilletia foetida.

NS-Róna 2 type winter wheat seeds infected with Fusarium spp. in 50.5% were infected with 0.2% by weight of Tilletia foetida spora calculated for the weight of the wheat.

incubated on Papavizas-type selective medium at 20° C. for 8 days and the Fusarium spp. infection was determined according to the developed sporulation and expressed in %.

Another part of the seeds was seeded on November 17 to plots of 2 m² prepared previously. 150 seeds were seeded to each line. The extent of the Tilletia foetida infection was determined on July 2 in the period of complete maturity by counting the ears one by one.

The results obtained by randomised block design method in three replicates are listed in Table 8.

The results show, that the combinations exhibit synergistic activity in the range of a weight ratio of 3:1 to 1:3 of carbendazime and the metal complexes; they reduce the Fusarium spp. infection and the Tilletia foetida infection to 0. The fungicidal activity thereof exceeds that of Quinolate V-4X.

TABLE 8

| Treatment | Dosage g/t | | | Rate of the active ingredients | Fusarium spp. infection % (laboratory) | Number of the ears/plot infected with Tilletia foetida |
|---|---|---|---|---|---|---|
| | Carboxin | Zn | Mn | | | |
| Carboxin | 900 | — | — | — | 31.0 | 3 |
| (8-oxyquino-late-(dimethyl dithiocarbamate) Zn complex | — | 900 | — | — | 26.0 | 7 |
| (8-oxyquino-late)-(dimethyl dithiocarbamate) Mn complex | — | — | 900 | — | 22.5 | 4 |
| zinc and | — | 225 | 675 | 1:3 | 18.0 | 5 |
| manganese | — | 450 | 450 | 1:1 | 13.5 | 3 |
| complex | — | 675 | 225 | 3:1 | 20.2 | 2 |
| Carboxin + | 225 | 338 | 337 | 1:3 | 0 | 0 |
| zinc and | 300 | 300 | 300 | 1:2 | 0 | 0 |

TABLE 8-continued

| Treatment | Dosage g/t Carboxin | Zn | Mn | Rate of the active ingredients | Fusarium spp. infection % (laboratory) | Number of the ears/plot infected with Tilletia foetida |
|---|---|---|---|---|---|---|
| manganese | 450 | 225 | 225 | 1:1 | 0 | 0 |
| complexes | 600 | 150 | 150 | 2:1 | 0 | 0 |
| in 1:1 ratio | 675 | 112 | 113 | 3:1 | 0 | 0 |
| infected with *ustilaginales* Control | — | — | — | — | 50.5 | 93 |
| Non-infected control | — | — | — | — | 49.8 | 10 |
| Ouinolate V-4X | 900 | — | — | — | 17.5 | 4 |

EXAMPLE 9

Winter barley was seed-dressed against the infection of Fusarium spp., Aspergilus, Penicillium and *Tilletia foetida*. The experiments were carried out similarly to Example 8, the combinations described in Example 3 were used and Quinolate V-4X (15% of oxyquinolate copper complex+50% of carboxine) well known in the art was applied as control.

The experimental results are listed in Table 9.

The test results show, that the combinations according to the invention in the weight ratio of 1:3 to 3:1 of the active ingredients exhibit synergistic activity, they supress the Fusarium spp. and Aspergilus infection below 2%, while completely control the Penicillium and *Tilletia foetida* infection. Their antifungal effect is significantly higher than that of Quinolate V-4X widely used as a fungicide.

TABLE 9

| Treatment | Dosage g/t Carboxin | Zn | Mn | Rate of the active ingredients | Infection with Fusarium spp. (%) | Infection with Aspergilus (%) | Infection with Penicillium (%) | Number of the ears per plots infected with Tilletia foetida |
|---|---|---|---|---|---|---|---|---|
| Carboxin | 1800 | — | — | — | 30.4 | 20.7 | 17.6 | 0.6 |
| (8-oxyquinolate)- (dimethyl di- thiocarbamate) Zn complex | — | 1800 | — | — | 27.1 | 17.3 | 15.2 | 0.7 |
| (8-oxyquinolate)- (dimethyl di- thiocarbamate) Mn complex | — | — | 1800 | — | 23.2 | 12.9 | 10.3 | 0.4 |
| the mixture of | — | 450 | 1350 | 1:3 | 18.7 | 9.3 | 8.1 | 0.7 |
| the zinc and | — | 900 | 900 | 1:1 | 13.0 | 7.5 | 6.5 | 0.5 |
| manganese complexes | — | 1350 | 450 | 3:1 | 16.5 | 8.4 | 9.0 | 0.3 |
| Carboxin + | 450 | 675 | 675 | 1:3 | 0 | 0 | 0 | 0 |
| zinc and | 600 | 600 | 600 | 1:2 | 0.5 | 0 | 0 | 0 |
| manganese | 900 | 450 | 450 | 1:1 | 0.94 | 0.7 | 0 | 0 |
| complex | 1200 | 300 | 300 | 2:1 | 1.0 | 0.9 | 0 | 0 |
|  | 1350 | 225 | 225 | 3:1 | 1.36 | 1.2 | 0 | 0 |
| untreated control | — | — | — | — | 50.3 | 40.5 | 32.4 | 10.8 |
| Quinolate V-4X | 2000 | — | — | — | 8.0 | 14.4 | 6.0 | 2.5 |

EXAMPLE 10

Seed-dressing of peas against Fusarium spp., Alternaria, Penicillium and Aspergilus.

We proceed as disclosed in Example 8 but incubation is carried out for 10 days instead of 8. Compositions of Example 1 were used for dressing at a dose of 900 g/t. As comparison Orthocid 50 WP (50% Captane) was used similarly at a dose of 900 g/t. Results are shown in Table 10.

TABLE 10

| Treatment | Dose g/t | Active ingredient rate | Fusarium spp. infection % | Alternaria infection % | Penicillium infection % | Aspergilus infection % |
|---|---|---|---|---|---|---|
| Carboxin | 900 | — | 4.0 | 1.8 | 3.0 | 4.2 |
| Zn complex | 900 | — | 2.7 | 1.7 | 1.5 | 1.8 |
| Mn complex | 900 | — | 2.3 | 1.3 | 1.0 | 1.5 |
| mixture of zinc and manganese complexes | 900 | 1:3 | 1.9 | 0.9 | 0.8 | 1.3 |
| composition according to the invention | 900 | 1:2 | 0 | 0. | 0 | 0 |
|  | 900 | 1:1 | 0 | 0 | 0 | 0 |
|  | 900 | 2:1 | 0 | 0 | 0 | 0 |
|  | 900 | 3:1 | 0 | 0 | 0 | 0 |
| untreated control | — | — | 9.5 | 4.5 | 12.0 | 9.5 |

TABLE 10-continued

| Treatment | Dose g/t | Active ingredient rate | Fusarium spp. infection % | Alternaria infection % | Penicillium infection % | Aspergilus infection % |
|---|---|---|---|---|---|---|
| Orthocid 50 WP | 900 | — | 1.0 | 2.0 | 2.0 | 3.5 |

Test results show the efficient protective activity against the four types of fungi by using a 3:1–1:3 mixture of Carboxin and zinc and manganese complexes (1:1 mixture) of (8-oxyquinolate)-(dimethyl-dithiocarbamate).

The compositions according to the invention are further suitable against the following fungi: *Ustilago triciti* (wheat), *Ustilago hordei* (barley), *Ustilago avenae* (oats) and Septorium, Fusarium and Penicillium of corn, wheat, barley and oat. Good results were obtained against Rhizoctonia infection of potato buds and seeds and fusarium tilting of scotch fir and black pine.

The chemical names and producers of the additives used in Examples 1 to 5 are as follows:

| Trade name | Producer | Chemical name |
|---|---|---|
| Tamol MD | BASF | sodium salt of a copolymer of maleinic acid and olephine |
| Pluriol PE 10500 | BASF | condensating product of ethylene oxide and propylene oxide |
| Poligen ASN | BASF | acrylate-styrene copolymer |
| Rhodamin 2BU Flu | BASF | xanthene type lye |
| Borresperse 3A | Borresgaard | sodium lignine sulphonate |
| Tensiofix CD5 | Tensia | cocoanut alcohol polyglycol ether |
| Rhodopol 23 | Rhone-Poulenc | polysacharide |
| Netzer IS | Hoechst | aliphatic sulphonic acid Na |
| Dispergermittel 1494 | | cresol-formaldehyde condensate |
| Tensiofix AS | Tensia | octylphenol-polyglycol-ether |
| Tensiofix IS | Tensia | nonylphenol-polyglycol-ether |

We claim:

1. A synergistic fungicidal composition effective against *Ustilago nuda* which comprises a fungicidally, synergistically effective amount of:
   (a) 2,3-dihydro-6-methyl-5-phenylcarbamoyl-1,4-oxathiin;
   (b) zinc-(8-oxiquinolinate)-dimethyl-dithiocarbamate complex; and
   (c) manganese-(8-oxyquinolinate)-dimethyl-dithiocarbamate complex;
   wherein the weight ratio between the 2,3-dihydro-6-methyl-5-phenyl-carbamoyl-1,4-oxathiin and the combined zinc and manganese complexes is 1:2 to 3:1 and the weight ratio of the zinc complex to the manganese complex is 1:1.

2. A method of treating the *Ustilago nuda* fungal infection in spring barley which comprises the step of applying a fungicidally effective amount of the synergistic fungicidal composition defined in claim 1 to the locus of the fungal infection.

3. A synergistic fungicidal composition effective against *Puccinia glumarum* which comprises a fungicidally, synergistically effective amount of:
   (a) 2,3-dihydro-6-methyl-5-phenylcarbamoyl-1,4-oxathiin-4,4-dioxide;
   (b) zinc-(8-oxyquinolinate)-dimethyl-dithiocarbamate complex; and
   (c) manganese-(8-oxyquinolinate)-dimethyl-dithiocarbamate complex;
   wherein the weight ratio between the 2,3-dihydro-6-methyl-5-phenyl-carbamoyl-1,4-oxathiin-4,4-dioxide and the combined zinc and manganese complexes is 1:3 to 3:1 and the weight ratio of the zinc complex to the manganese complex is 1:1.

4. A method of treating a *Puccinia glumarum* infection in winter wheat which comprises the step of applying a fungicidally effective amount of the synergistic fungicidal composition defined in claim 3 to the locus of the fungal infection.

5. A synergistic fungicidal composition effective against *Tilletia foetida,* Fusarium spp., Aspergilus, Penicillium, or Alternaria, which comprises a fungicidally, synergistically effective amount of:
   (a) 2,3-dihydro-6-methyl-5-phenylcarbamoyl-1,4-oxathiin;
   (b) zinc-(8-oxyquinolinate)-dimethyl-dithiocarbamate complex; and
   (c) manganese-(8-oxyquinolinate)-dimethyl-dithiocarbamate complex; wherein the weight ratio between the 2,3-dihydro-6-methyl-5-phenyl-carbamoyl-1,4-oxathiin and the combined zinc and manganese complexes is 1:3 to 3:1 and the weight ratio of the zinc complex to the manganese complex is 1:1.

6. A method of treating a Fusarium spp. infection or a *Tilletia foetida* infection in winter wheat which comprises the step of applying a fungicidally effective amount of the synergistic fungicidal composition defined in claim 5 to the locus of the fungal infection.

7. A method of treating a Fusarium spp. infection, Aspergilus infection, Penicillium infection, or *Tilletia foetida* infection in winter barley which comprises the step of applying a fungicidally effective amount of the synergistic fungicidal composition defined in claim 5 to the locus of the fungal infection.

8. A method of treating a Fusarium spp. infection, Alternaria infection, Penicillium infection, or Aspergilus infection in pea plants which comprises the step of applying a fungicidally effective amount of the synergistic fungicidal composition defined in claim 5 to the locus of the fungal infection.

* * * * *